US00PP36060P3

(12) United States Plant Patent
Kuji et al.

(10) Patent No.: US PP36,060 P3
(45) Date of Patent: Aug. 6, 2024

(54) HOP PLANT NAMED 'FURANO 0414B Go'

(50) Latin Name: ***Humulus lupulus* L.**
Varietal Denomination: Furano 0414B Go

(71) Applicant: Sapporo Breweries Limited, Tokyo (JP)

(72) Inventors: Seigi Kuji, Tokyo (JP); Yutaka Itoga, Tokyo (JP); Koichiro Koie, Tokyo (JP); Mitsuhiro Uemoto, Tokyo (JP); Yuto Furukawa, Tokyo (JP); Masanobu Goto, Tokyo (JP); Katsuyoshi Shimaoka, Tokyo (JP)

(73) Assignee: SAPPORO BREWERIES LIMITED, Tokyo (JP)

( * ) Notice: Subject to any disclaimer, the term of this patent is extended or adjusted under 35 U.S.C. 154(b) by 0 days.

(21) Appl. No.: 18/086,014

(22) Filed: Dec. 21, 2022

(65) Prior Publication Data

US 2023/0210036 P1 Jun. 29, 2023

(30) Foreign Application Priority Data

Dec. 24, 2021 (JP) ..... 35915

(51) Int. Cl.
*A01H 5/02* (2018.01)
*A01H 6/00* (2018.01)
*A01H 6/28* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 6/28
See application file for complete search history.

(56) References Cited

U.S. PATENT DOCUMENTS

PP30,067 P3 * 1/2019 Koie ..... A01H 6/28
Plt./236

* cited by examiner

*Primary Examiner* — June Hwu
(74) *Attorney, Agent, or Firm* — Weatherly IP Solutions, LLC; James M. Weatherly

(57) ABSTRACT

A new hop plant particularly distinguished by having a cylindrical to club plant shape, an alpha acids in cones of 8.7%, cohumulone ratio to alpha acids of 20.7%, myrcene ratio to total oil of 63.1% and a farnesene ratio to total oil of 2.9% as well as a fruit and flower flavor, is disclosed.

2 Drawing Sheets

Genus and species: *Humulus lupulus* L.
Variety denomination: 'Furano 0414B Go'.

CROSS-REFERENCE TO RELATED APPLICATION

This patent application claims the benefit of priority from Japan Plant Breeders Rights Application No. 35915 as filed on Dec. 24, 2021, the contents of which is incorporated herein by reference for all it teaches and discloses.

BACKGROUND OF THE NEW PLANT

The present invention comprises a new and distinct variety of Hop, botanically known as *Humulus lupulus* L. and hereinafter referred to by the variety name 'Furano 0414B Go'. 'Furano 0414B Go' is a selection from a controlled cross of the commercial hop female parent 'Little Star' (unpatented) and the proprietary male parent '980573' (unpatented).

The commercial female hop line 'Little Star' and the proprietary male hop line '980573' were cross-pollinated in 2001 in Kamifurano-cho, Sorachi-gun, Hokkaido, Japan and seeds were obtained. The seeds were sown and plants were grown for evaluation. A plant line was selected in March of 2003 in Kamifurano-cho, Sorachi-gun, Hokkaido, Japan and named 'Furano 0414B Go'. In 2005, 'Furano 0414B Go' was first vegetatively propagated by in Kamifurano, Hokkaido, Japan via vegetative cuttings. 'Furano 0414B Go' was found to reproduce true to type in successive generations of asexual propagation via vegetative cuttings in Kamifurano, Hokkaido, Japan.

SUMMARY

The following are the most outstanding and distinguishing characteristics of this new variety when grown under normal horticultural practices in Kamifurano, Hokkaido, Japan.

1. Cylindrical to club plant shape;
2. An alpha acids in cones of 8.7%;
3. A cohumulone ratio to alpha acids of 20.7%;
4. A myrcene ratio to total oil of 63.1%;
5. A farnesene ratio to total oil of 2.9%; and
6. A fruit and flower flavor.

DESCRIPTION OF THE PHOTOGRAPHS

This hop plant is illustrated by the accompanying photographs which show the plant's overall plant shape, leaf shape and cone shape. FIGS. 1 and 3 are of a three-year-old plant grown in Kamifurano, Hokkaido, Japan in August 2020 while FIG. 2 is also of a four-year-old plant grown in Kamifurano, Hokkaido, Japan taken in August 2021. The colors shown are as true as can be reasonably obtained by conventional photographic procedures.

DESCRIPTION OF THE NEW VARIETY

Figure 1:
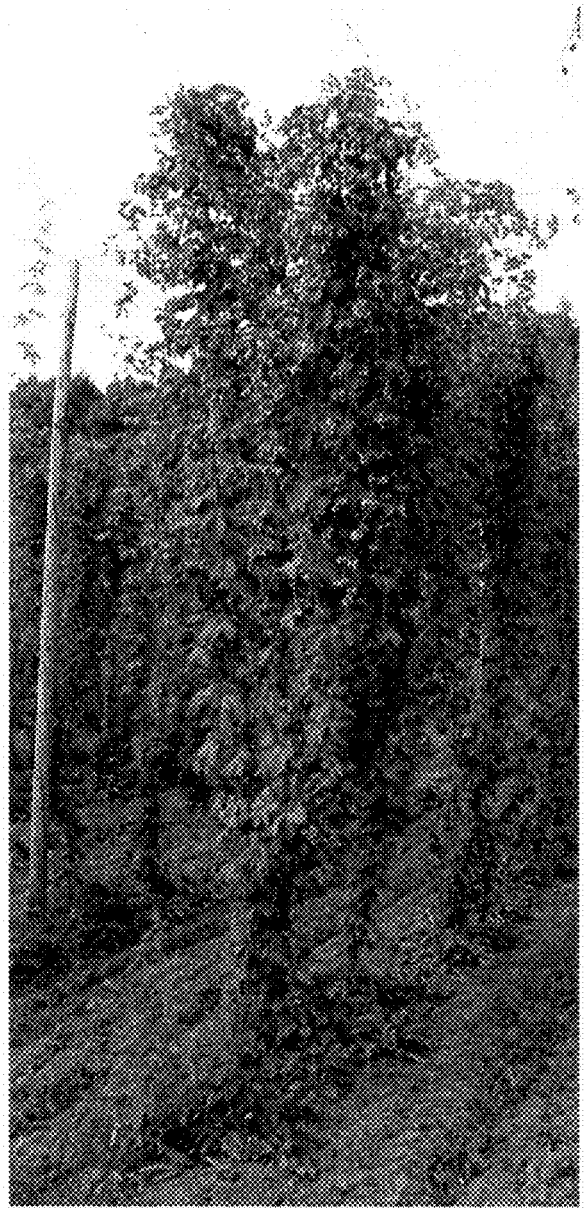
FIG. 1 shows the plant shape of 'Furano 0414B Go'.
Figure 2:
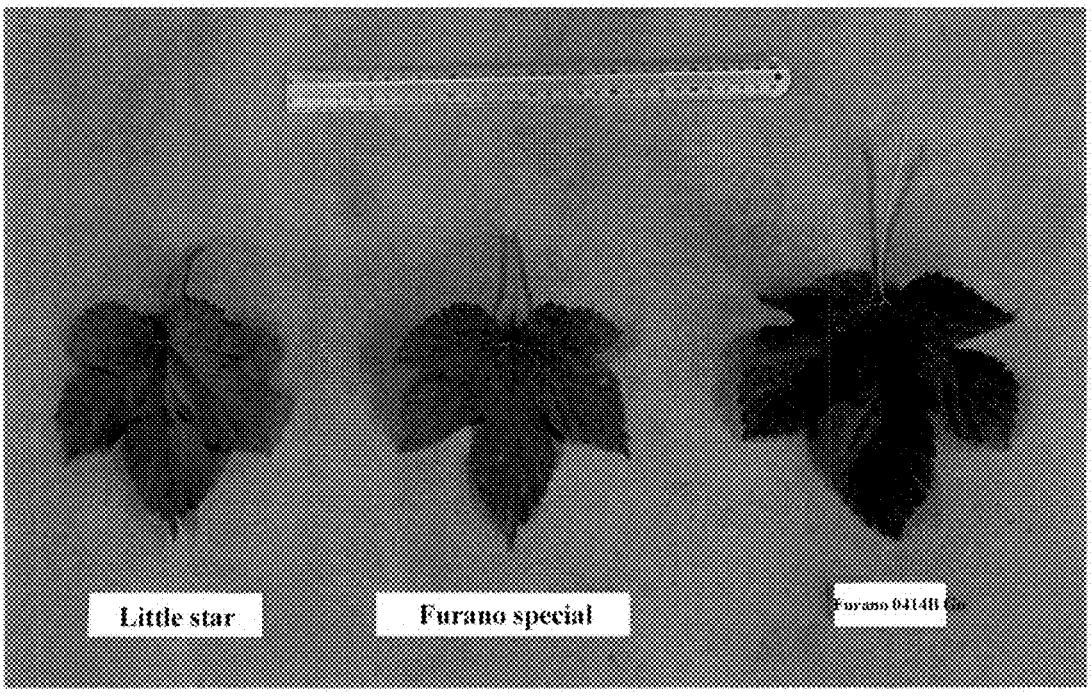
FIG. 2 shows the leaf shape of 'Furano 0414B Go' together with that of 'Little Star' and 'Furano Special' in the left and in the middle, respectively.
Figure 3:
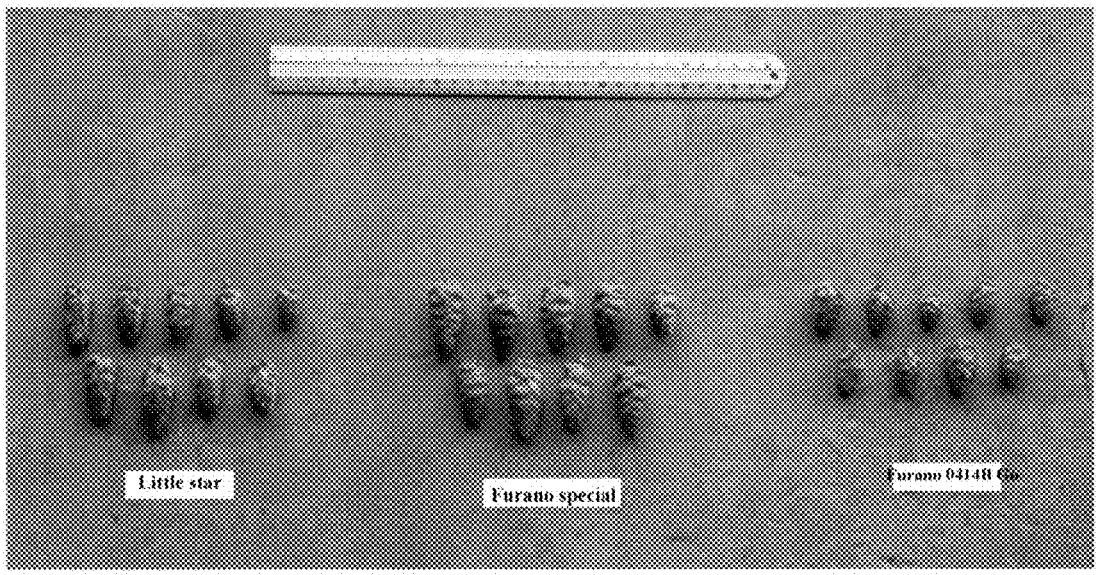
FIG. 3 shows the cone shape of 'Furano 0414B Go' together with that of 'Little Star' and 'Furano Special' in the left and in the middle, respectively.

The following detailed descriptions set forth the distinctive characteristics of 'Furano 0414B Go'. The data, which define these characteristics, were collected from asexual reproductions carried out in Kamifurano, Hokkaido, Japan. Data was collected on three-year-old plants in Kamifurano, Hokkaido, Japan in 2020 or 2023. Color references are to Japan Horticultural Plant Color Chart (1987, Japan Color Research Institute).

Classification:

*Family*.—Cannabaceae.

*Classification*.—*Humulus lupulus* L.

*Common name*.—Hop.

Parents:

*Female parent*.—'Little Star' (unpatented).

*Male parent*.—'980573' (unpatented).

Propagation:

*Type*.—Vegetative cuttings or rhizomes.

Plant description:

*Plant and growth habit*.—The plant growth type is normal, not dwarf.

*Plant shape*.—Cylindrical to club.

*Plant height*.—Hop plants were grown at a trellis of 5.5 m high.

*Plant head volume*.—Medium.

*Anthocyanin*.—Anthocyanin coloration of the main bine is medium.

*Anthocyanin color*.—Dark red purple (9510).

Lateral branch description:

*Length*.—The average length of lateral branches is 97.9 cm, ranged between 42.1-166.0 cm.

*Diameter*.—The average diameter of lateral branches is 0.35 cm, ranged between 0.30-0.38 cm.

*Internode length*.—The average internode length of lateral branches is 11.6 cm, ranged between 6.0-25.0 cm.

*Color, fully developed* (*mature*).—Upper surface is bright yellow green (3504), and lower surface is strong red purple (9214).

Foliage description:

*Arrangement*.—Opposite.

*Length*.—The average length of foliage is 15.3 cm, ranged between 13.0-17.0 cm.

*Width*.—The average width of foliage is 15.2 cm, ranged between 12.5-16.5 cm.

*Shape*.—Palmate, 3 to 5 lobes.

*Apex*.—Cuspidate.

*Base*.—Cordate.

*Margin*.—Serrate.

*Texture*.—Upper surface: Blistering of upper side of blade is slightly strong.

*Color*.—Fully expanded (mature) leaves: Upper surface: Dark green (3707). Lower surface: Dull yellow green (3514).

*Foliage density*.—The foliage density of side shoot from middle third of plant is little sparse.

*Stipule*.—Number: Two stipules per node. Color: Vivid yellow green (3506). Direction: Upward.

Petiole:

*Length*.—The average length of petioles is 6.9 cm, ranged between 6.0-8.0 cm.

*Diameter*.—The average diameter of petioles is 0.34 cm, ranged between 0.31-0.38 cm.

*Color*.—Upper and lower surfaces: Light yellow green (3503).

Flower description:

*Cones*.—Number of cones per lateral branch from middle of plant is few (average: 34.9 cones/branch, ranged from 20-49). Number of cones per node of lateral branches from middle of plant is slightly few (average: 6.4 cones/node, ranged from 3.5-12.3). Number of cones per lateral branch from upper third of plant is quite many (average: 110.2 cones/branch ranged between 26-420).

*Time of flowering*.—Slightly early (early July).

*Time of picking maturity of cones*.—Medium (end of August).

Pistillate inflorescence:

*Average size*.—The average diameter of Pistillate inflorescence is 1.1 cm.

*Number of flower pairs in cluster*.—The average number of flower pairs in cluster is 5.6.

*Size of bracts at based of flower*.—The average size of bracts at based of flower is 0.28 cm.

*Color of bracts*.—Bright yellow green (3505).

Inflorescence buds:

*Length*.—The average length of cones is 3.3 cm, ranged between 2.4-3.8 cm.

*Diameter*.—The average diameter of cones is 2.0 cm, ranged between 1.5-2.4 cm.

*Shape*.—The shape of cones is medium ovate, degree of opening bracts is slightly opened.

*Color*.—Deep yellow green (3307) and bright yellow green (3504).

Spike bracts:

*Length*.—The average length of spike bracts is 1.3 cm, ranged between 1.0-1.7 cm.

*Width*.—The average width of spike bracts is 1.1 cm, ranged between 0.9-1.2 cm.

*Shape*.—The shape is obtuse, and the width/length ratio is very large (average width/length ratio of bracts is 0.86, ranged between 0.71-1.09).

*Apex*.—The shape of apex is apiculate, and the length of apex of bract is medium.

*Margin*.—Entire.

*Color*.—Upper surface: Deep yellow green (3307). Lower surface: Bright yellow green (3505).

Bracteoles:

*Length*.—The average length of bracteoles is 1.1 cm, ranged between 1.0-1.3 cm.

*Width*.—The average width of bracteoles is 0.7 cm, ranged between 0.6-0.8 cm.

*Shape*.—The average width/length ratio is 0.59, ranged between 0.50-0.73.

*Shape*.—Narrow ovate.

*Apex*.—Obtuse.

*Margin*.—Entire.

*Color*.—Upper surface: Bright yellow green (3504). Lower surface: Light yellow green (3503).

Pedicels: Not observed.
Reproductive organs:
*Stamens*.—Not observed.
*Pistils*.—Not observed.
Disease and pest/insect resistance: Not resistant.
Brewing characteristics:
*Alpha acids content in cones*.—8.7%.
*Ratio of beta acids to alpha acids*.—1.00.
*Ratio of co-alpha to all alpha acids*.—0.21.
*Humulene ratio to total oil*.—0.20.
*Caryophyllene ratio to total oil*.—0.10.
*Humulene ratio to caryophyllene*.—2.02.
*Myrcene ratio to total oil*.—0.63.
*Farnesene ratio to total oil*.—0.03.
*Linalool ratio to total oil*.—0.01.
*Remaining rate of alpha acids after 6 months storage at room temperature*.—56.2%.
*Yield per hectare*.—1.86 t/ha.
*Flavor profile*.—Fruits, flower.

COMPARISON WITH PARENTAL LINES AND KNOWN VARIETY

'Furano 0414B Go' is a distinct variety of hop. 'Furano 0414B Go' is distinguished from its female parent 'Little Star' and the male parent '980573' as described in Table 1:

TABLE 1

Comparison with Parental Lines

| Characteristic | Variety 'Furano 0414B Go' | Female parent 'Little Star' | Male Parent '980573' |
|---|---|---|---|
| Flower | Produce female flowers and cones | Produce female flowers and cones | Does not produce any cones, but produce male flower |

TABLE 1-continued

Comparison with Parental Lines

| Characteristic | Variety 'Furano 0414B Go' | Female parent 'Little Star' | Male Parent '980573' |
|---|---|---|---|
| Alpha acids in cones | 8.7% | 4.9% | — |
| Cohumulone ratio to alpha acids | 20.7% | 25.3% | — |
| Farnesene ratioto total oil | 2.9% | 17.9% | — |

'Furano 0414B Go' is distinguished from the commercial hop variety 'Furano K906901060 go', commercially named 'Furano Magical' (U.S. Plant Pat. No. 30,067). Differences between the two varieties are described in Table 2:

TABLE 2

Comparison with Similar Variety

| Characteristic | Variety 'Furano 0414B Go' | Commercial line 'Furano K906901060 go' |
|---|---|---|
| Alpha acids in cones | 8.7% | 5.4% |
| Cohumulone ratio to alpha acids | 20.7% | 16.6% |
| Myrcene ratioto total oil | 63.1% | 31.7% |
| Farnesene ratioto total oil | 2.9% | 0.8% |

I claim:

1. A new and distinct cultivar of HOP PLANT NAMED 'FURANO 0414B GO' as described and illustrated herein.

* * * * *